(12) United States Patent
Sekiya et al.

(10) Patent No.: US 8,449,743 B2
(45) Date of Patent: May 28, 2013

(54) GAS SENSOR

(75) Inventors: Takayuki Sekiya, Nisshin (JP); Kei Kosaka, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 198 days.

(21) Appl. No.: 12/853,539

(22) Filed: Aug. 10, 2010

(65) Prior Publication Data

US 2011/0036716 A1    Feb. 17, 2011

(30) Foreign Application Priority Data

Aug. 17, 2009    (JP) ................................. 2009-188212

(51) Int. Cl.
*G01N 27/407*    (2006.01)
(52) U.S. Cl.
USPC ......... 204/428; 73/23.31; 73/23.32; 204/424; 204/425; 204/426; 204/427; 204/429
(58) Field of Classification Search
USPC .............. 204/424–429; 205/781, 783.5–785; 73/23.31–23.32
See application file for complete search history.

(56) References Cited

U.S. PATENT DOCUMENTS

| | | | |
|---|---|---|---|
| 5,012,670 A | 5/1991 | Kato et al. | |
| 5,238,552 A | 8/1993 | Kato et al. | |
| 5,948,963 A | 9/1999 | Kato et al. | |
| 6,346,179 B1 | 2/2002 | Makino et al. | |
| 6,348,141 B1 | 2/2002 | Kato et al. | |
| 6,432,289 B1 * | 8/2002 | Uchida et al. | 204/428 |
| 2003/0019280 A1 | 1/2003 | Toguchi et al. | |
| 2004/0144645 A1 | 7/2004 | Yamada et al. | |
| 2006/0108222 A1 | 5/2006 | Yamada et al. | |
| 2008/0236248 A1 | 10/2008 | Ikoma et al. | |

FOREIGN PATENT DOCUMENTS

| | | |
|---|---|---|
| EP | 1 046 906 A2 | 10/2000 |
| EP | 1 279 957 A2 | 1/2003 |
| EP | 1 918 699 A1 | 5/2008 |
| JP | 01-296159 A1 | 11/1989 |
| JP | 05-026842 A1 | 2/1993 |
| JP | 10-318980 A1 | 12/1998 |
| JP | 2000-171430 A1 | 6/2000 |
| JP | 2000-304719 A1 | 11/2000 |
| JP | 2001-074686 A1 | 3/2001 |
| JP | 2003-043002 A1 | 2/2003 |
| JP | 2003-107033 A1 | 4/2003 |
| JP | 2004-245828 A1 | 9/2004 |
| JP | 2004-301579 A1 | 10/2004 |
| JP | 2008-075634 A1 | 4/2008 |
| JP | 2009-097868 A1 | 5/2009 |

* cited by examiner

*Primary Examiner* — Keith Hendricks
*Assistant Examiner* — Bach Dinh
(74) *Attorney, Agent, or Firm* — Burr & Brown

(57) ABSTRACT

A gas sensor, that represses a manufacturing cost, obtains high responsiveness and can effectively reduce adhesion of water to a sensor element and intrusion of water into the sensor element, is provided. In the gas sensor that has the sensor element mainly containing a solid electrolyte with oxygen ion conductivity and a protective cover arranged to surround the sensor element and detects a predetermined gas component in a measurement gas, the protective cover includes an inner protective cover that is formed into a bottomed cylindrical shape, has a plurality of inner gas distributing holes formed in two rows on its side surface in a longitudinal direction of the sensor element and surrounds one front end of the sensor element, and an outer protective cover that is formed into a bottomed cylindrical shape, has a plurality of outer gas distributing holes on its side surface and surrounds the inner protective cover.

6 Claims, 10 Drawing Sheets

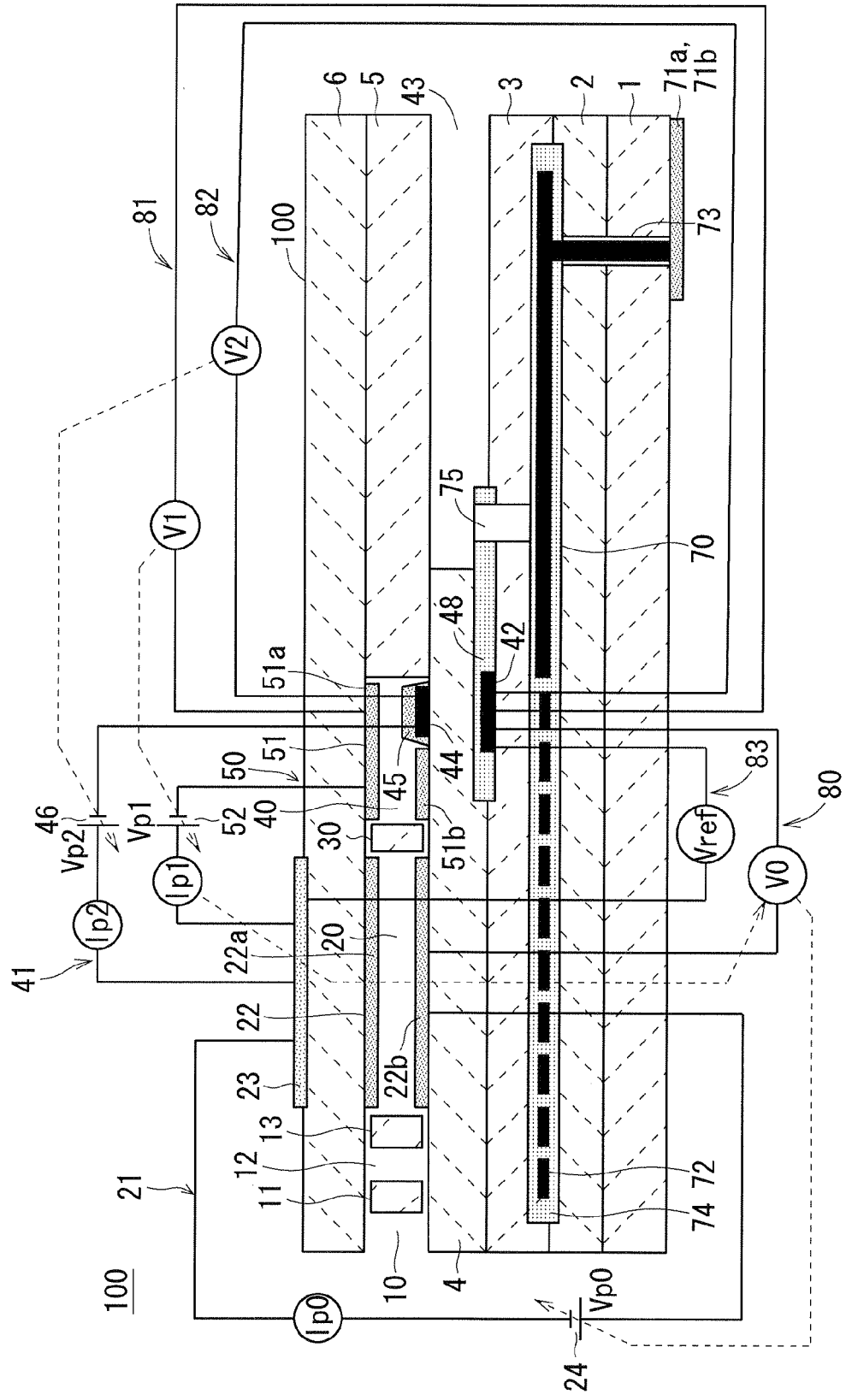
F I G . 2

GAS SENSOR A  AT THE TIME WHEN 20 ms ELAPSES:
REPLACE BY 65% IN PERIPHERY OF THE SENSOR ELEMENT FRONT END

GAS SENSOR C  AT THE TIME WHEN 20 ms ELAPSES:
REPLACE BY 60% IN PERIPHERY OF THE SENSOR ELEMENT FRONT END

GAS SENSOR A  AT THE TIME WHEN 40 ms ELAPSES:
REPLACE BY 85% IN PERIPHERY OF THE SENSOR ELEMENT FRONT END

GAS SENSOR C  AT THE TIME WHEN 40 ms ELAPSES:
REPLACE BY 80% IN PERIPHERY OF THE SENSOR ELEMENT FRONT END

GAS SENSOR A  AT THE TIME WHEN 60 ms ELAPSES:
REPLACE BY 95% IN PERIPHERY OF THE SENSOR ELEMENT FRONT END

GAS SENSOR C  AT THE TIME WHEN 60 ms ELAPSES:
REPLACE BY 85% IN PERIPHERY OF THE SENSOR ELEMENT FRONT END

F I G. 6 A
GAS SENSOR A    AT THE TIME WHEN 100 ms ELAPSES:
REPLACE BY 100% IN PERIPHERY OF THE SENSOR ELEMENT FRONT END
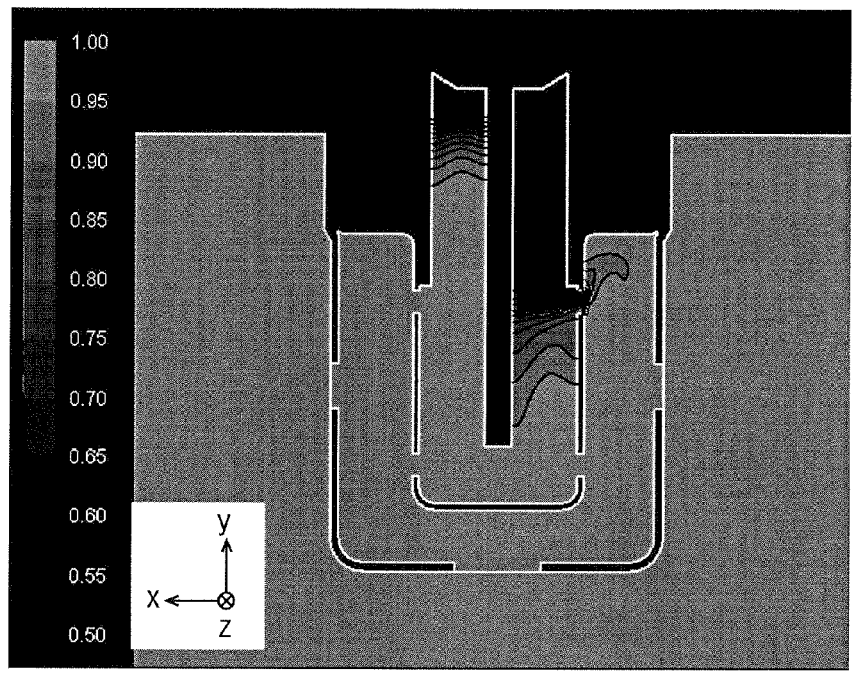
F I G. 6 B
GAS SENSOR C    AT THE TIME WHEN 100 ms ELAPSES:
REPLACE BY 90% IN PERIPHERY OF THE SENSOR ELEMENT FRONT END
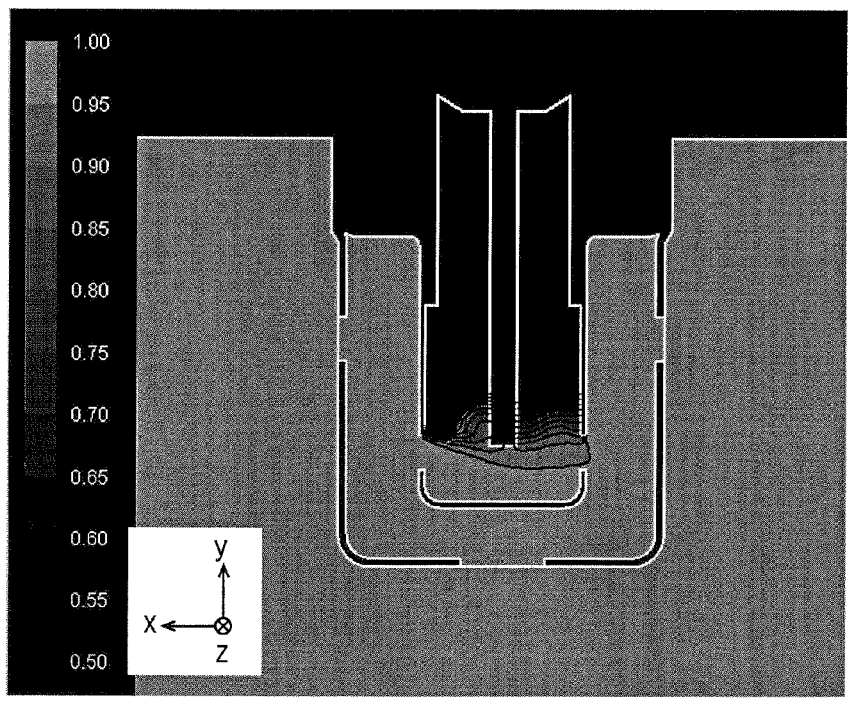

GAS SENSOR A AT THE TIME WHEN 200 ms ELAPSES:
REPLACE BY 100% IN PERIPHERY OF THE SENSOR ELEMENT FRONT END

GAS SENSOR C AT THE TIME WHEN 200 ms ELAPSES:
REPLACE BY 90% IN PERIPHERY OF THE SENSOR ELEMENT FRONT END

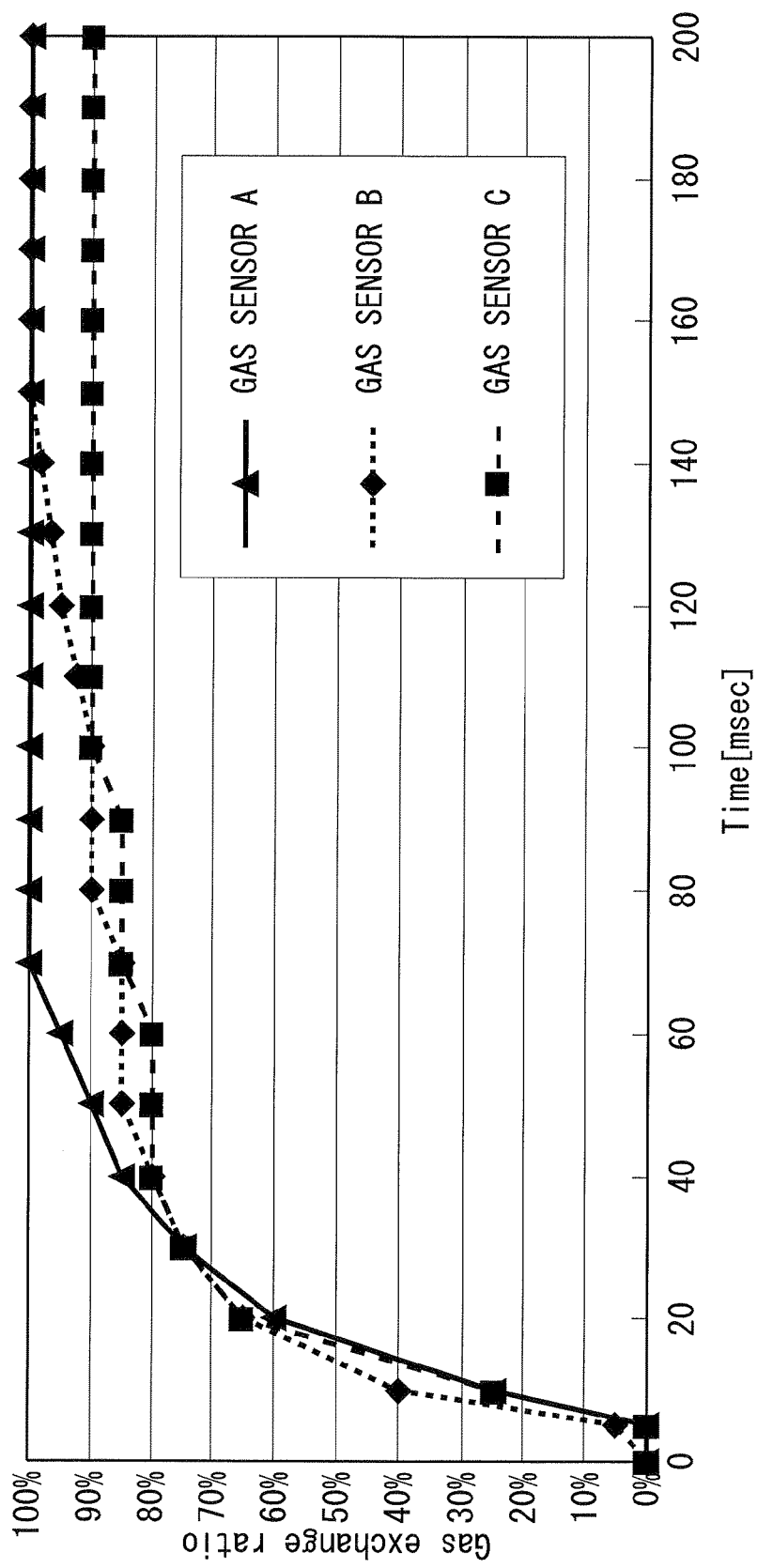

GAS SENSOR

CROSS-REFERENCE TO RELATED APPLICATION

This application claims the benefit of Japanese patent application number 2009-188212 filed on Aug. 17, 2009.

BACKGROUND OF THE INVENTION

1. Field of the Invention

The present invention relates to a gas sensor that has a sensor element and measures a predetermined gas component in a measurement gas. The invention particularly relates to a gas sensor that has a protective cover arranged so as to surround a sensor element.

2. Description of the Background Art

Conventionally, various measuring devices are used to know the concentration of a desired gas component in a measurement gas. For example, as devices that measure a NOx concentration in a measurement gas such as a combustion gas, gas sensors are publicly known that have an electrochemical pump cell structured by forming a Pt electrode and an Rh electrode on a solid electrolyte layer made of zirconia ($ZrO_2$) having oxygen ion conductivity.

Such gas sensors are used for measuring a desired gas component included in exhaust gases from automobiles. The gas sensors to be mounted into tail-pipes of automobiles are provided with protective covers for protecting sensor elements in order to mainly prevent adhesion of water generated at the time of engine starting to the sensor elements and prevent water intrusion into the sensor elements.

Such various protective covers are already publicly known. For example, a protective cover, in which a flow of measurement gases is a swirl flow in one direction, is publicly known (for example, refer to Japanese Patent Application Laid-Open No. 01-296159 (1989)). Further, a protective cover is also publicly known that represses occurrence of a crack on a sensor element due to the adhesion of water and a decrease in temperature of the sensor element due to a decrease in temperature of measurement gases (for example, refer to Japanese Patent Application Laid-Open No. 10-318980 (1998)).

Further, protective covers are also publicly known that adopt a triplex structure (an inner protective cover, an intermediate protective cover, and an outer protective cover) so as to effectively prevent the adhesion of water (for example, refer to Japanese Patent Application Laid-Open Nos. 2000-304719 and 2004-301579).

It is necessary for heightening the accuracy of gas sensors to heighten responsiveness, namely, enable the measurement of concentration quickly conforming with a concentration change of a predetermined gas component in a measurement gas and to reduce the adhesion of water to a sensor element generated at the time of engine starting.

In the case of the gas sensors having the protective covers, it is necessary for securing the responsiveness that atmospheres in the protective covers are quickly replaced by measurement gases present outside the protective covers.

However, to heighten a replacement property of the measurement gases in the protective covers conflicts with to reduce the adhesion of water to the sensor elements, and thus it is difficult to simultaneously realize both of them.

The protective covers disclosed in Japanese Patent Application Laid-Open Nos. 01-296159 and 10-318980 have the structure such that the reduction in the adhesion of water and the intrusion of water into the sensor elements is emphasized. For this reason, their responsiveness is not sufficient.

An object of the protective covers adopting the triplex structure disclosed in Japanese Patent Application Laid-Open No. 2000-301749 and Japanese Patent Application Laid-Open No. 2004-301579 is to effectively prevent the adhesion of water and simultaneously obtain high responsiveness. However, since the intermediate protective covers are provided, manufacturing steps become complicated and thus production cost becomes high.

SUMMARY OF THE INVENTION

The present invention is directed to a gas sensor that measures a predetermined gas component in measurement gas components, and particularly directed to provide a protective cover that is mounted to the gas sensor and arranged so as to surround a sensor element.

A gas sensor of the present invention includes a sensor element mainly containing solid electrolyte with oxygen ion conductivity, and a protective cover arranged to surround the sensor element that has an inner protective cover of a bottomed cylindrical shape that has a plurality of inner gas distributing holes formed in two rows on a side surface of the inner protective cover in a longitudinal direction of the sensor element and surrounds one end of the sensor element, and an outer protective cover of a bottomed cylindrical shape that has a plurality of outer gas distributing holes on a side surface of the outer protective cover and surrounds the inner protective cover.

Preferably, the plurality of inner gas distributing holes have a plurality of first inner gas distributing holes and a plurality of second inner gas distributing holes, the plurality of first inner gas distributing holes are formed on the side surface of the inner protective cover in a position on a bottom side of the inner protective cover with respect to a position opposed to one front end of the sensor element, the plurality of second inner gas distributing holes are formed on the side surface of the inner protective cover in a position on an other front end of the sensor element with respect to the position opposed to the one front end of the sensor element.

According to the present invention, when the first gas distributing holes and the second gas distributing holes are provided to the side surface of the inner protective cover, the gas sensor, that has excellent responsiveness and effectively prevents adhesion of water present in a pipe to the sensor element and intrusion of water present in the pipe into sensor element, is realized. Therefore, it is an object of the present invention to provide the gas sensor that represses a manufacturing cost, has high responsiveness and can effectively reduce the adhesion of water to the sensor element and the intrusion of water into the sensor element.

These and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a schematic view schematically illustrating one example of a configuration of a sensor element of the gas sensor according to the preferred embodiment of the present invention;

FIGS. 3A, 3B, 4A, 4B, 5A, 5B, 6A, 6B, 7A and 7B are diagrams illustrating results of responsiveness simulation of the gas sensor;

FIG. 8 is a diagram illustrating a result of the responsiveness simulation of the gas sensor;

DETAILED DESCRIPTION OF THE INVENTION

Preferred Embodiment

<Schematic Configuration of Gas Sensor>

At first, a schematic configuration of a gas sensor according to a preferred embodiment of the present invention is described.

Figure 1:
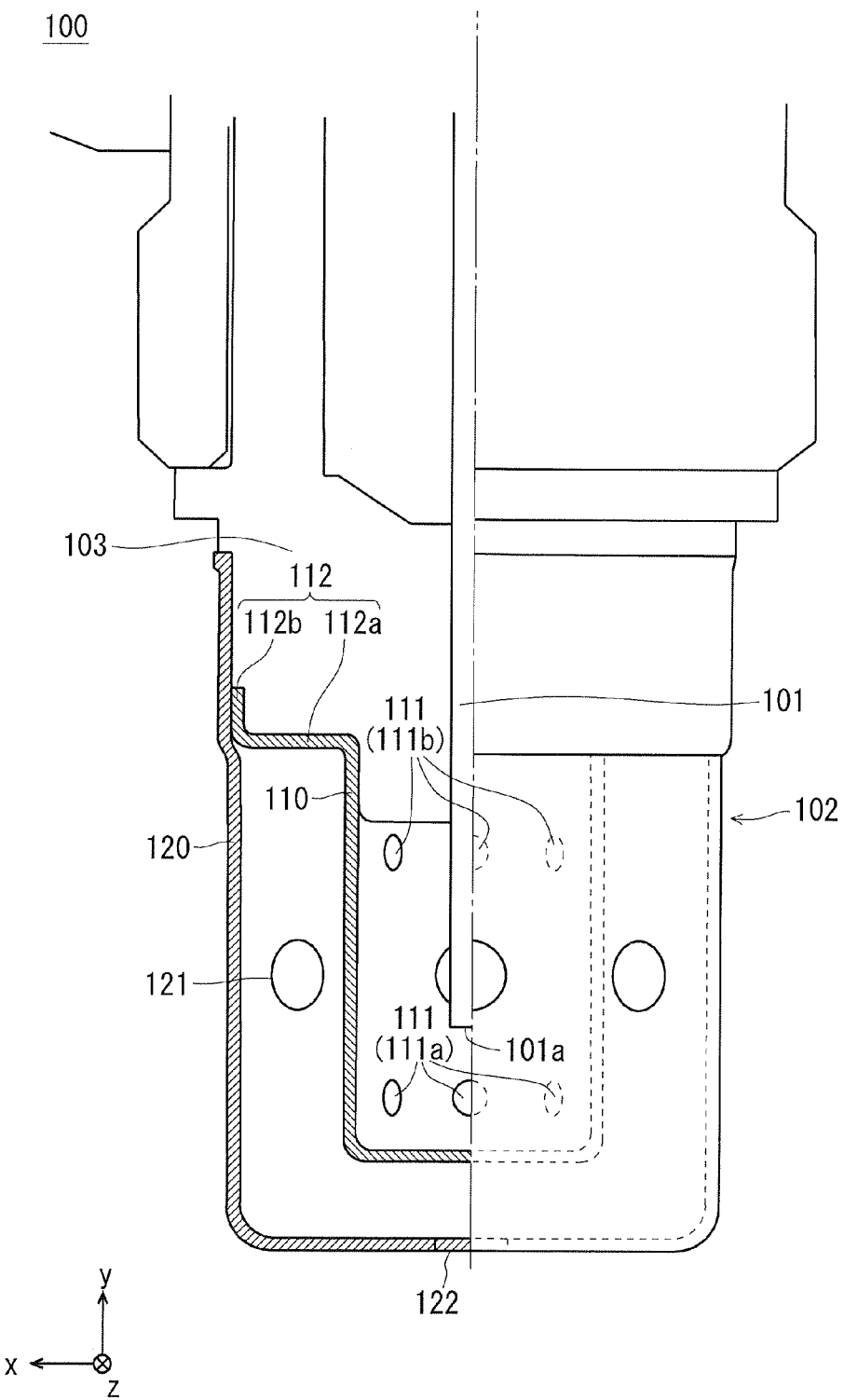
FIG. 1 is a partial cross sectional view schematically illustrating one example of a configuration of a gas sensor according to a preferred embodiment of the present invention.
Figure 3A:
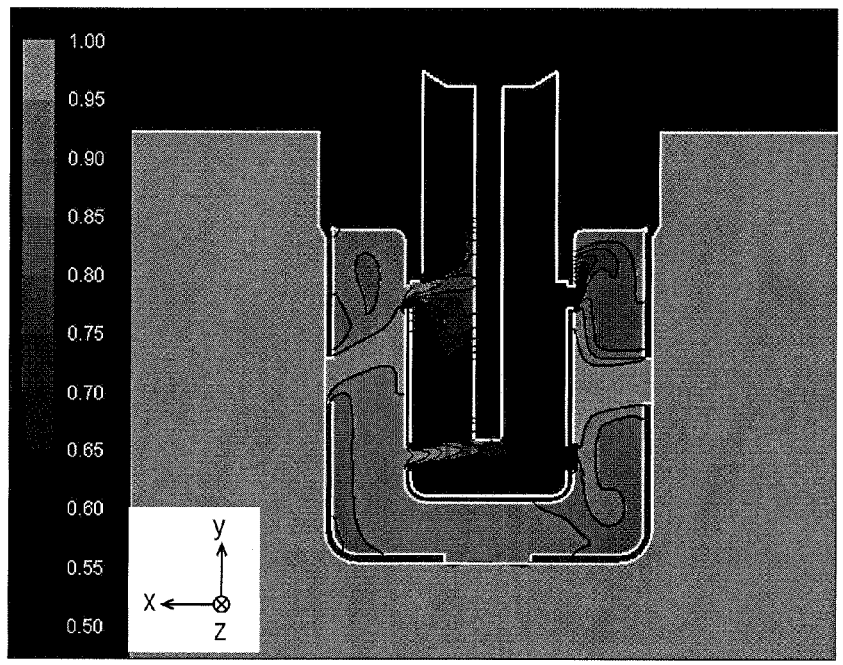
Figure 3B:
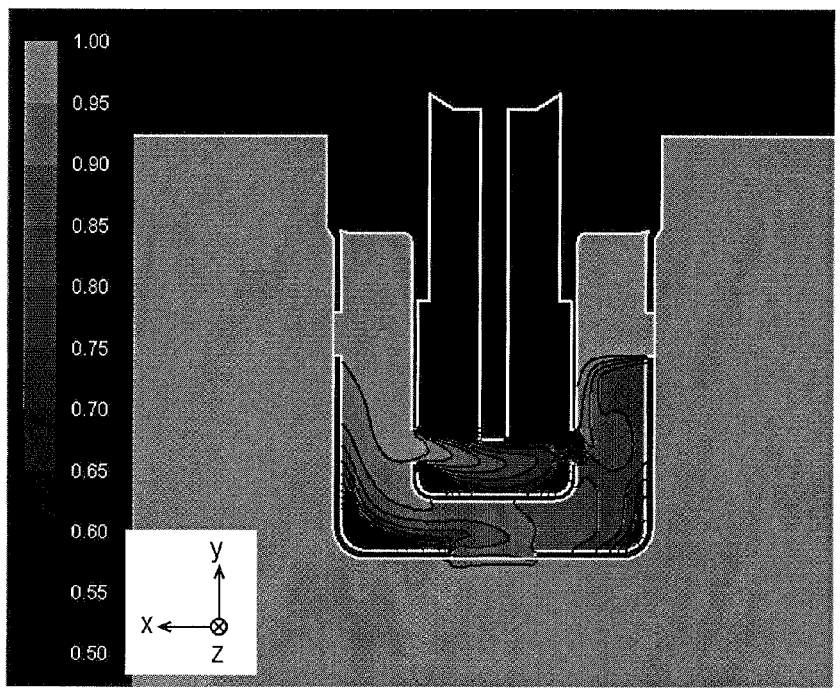
Figure 4A:
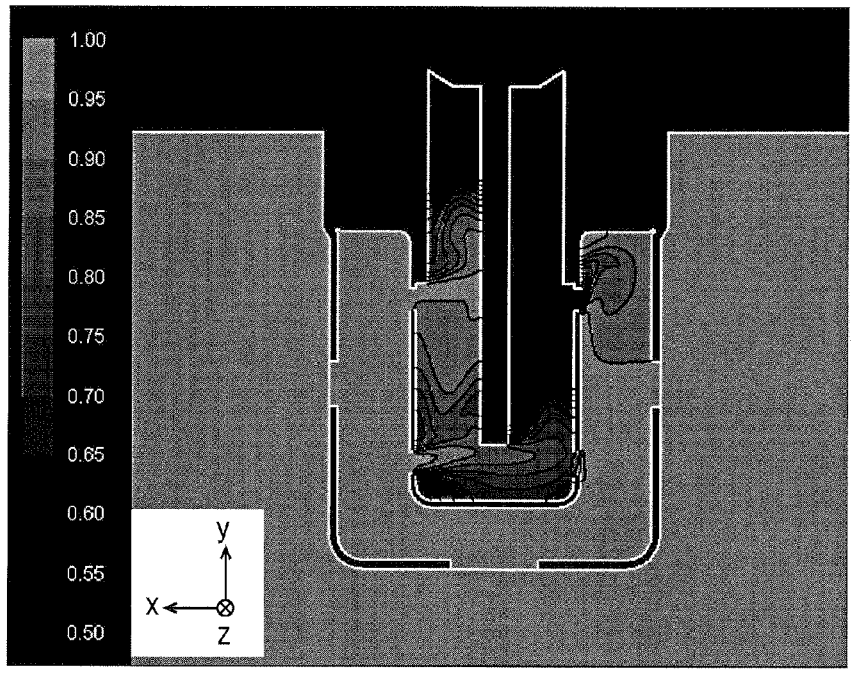
Figure 4B:
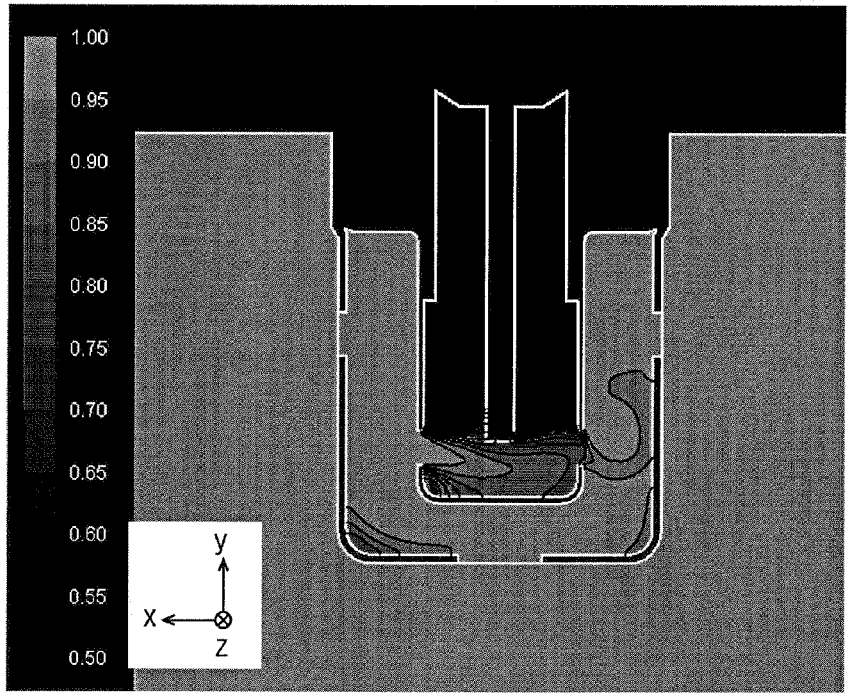
Figure 5A:
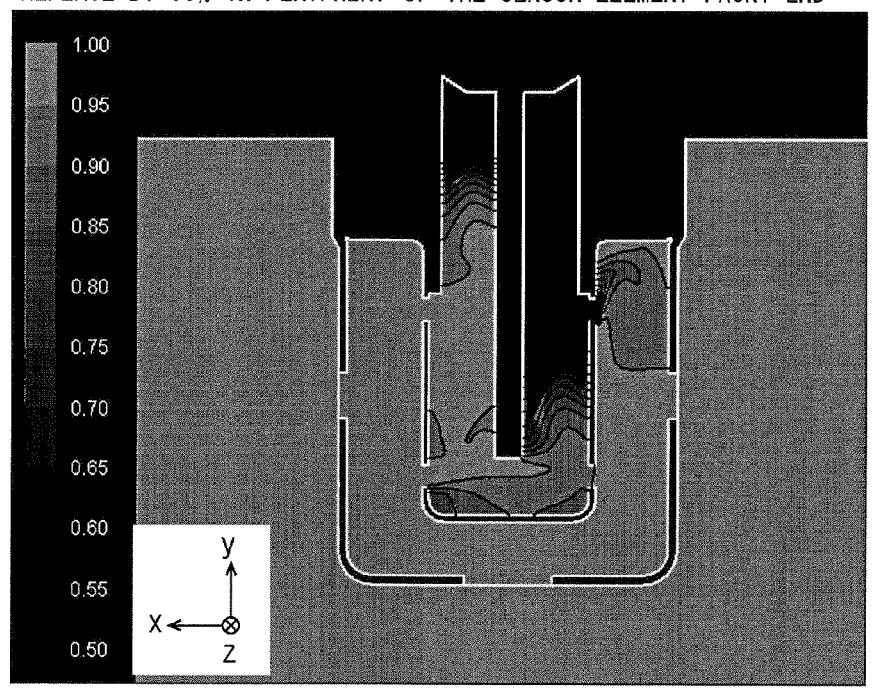
Figure 5B:
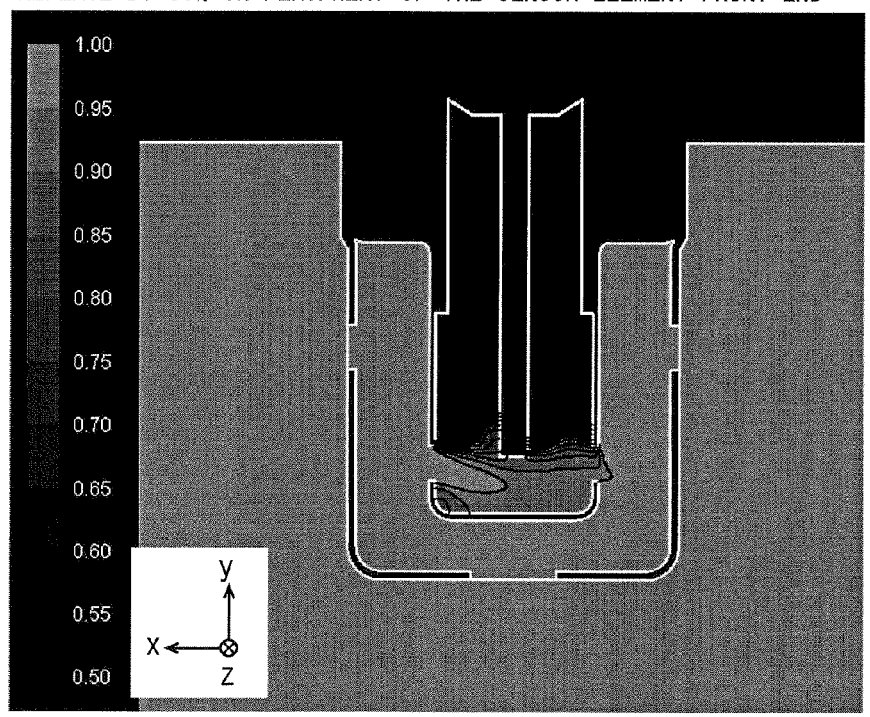
Figure 7A:
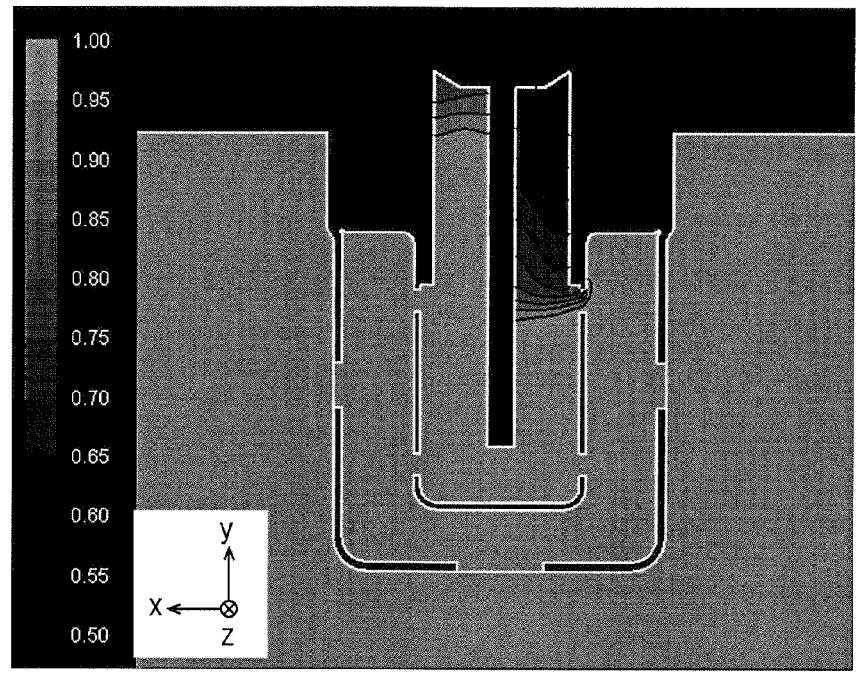
Figure 7B:
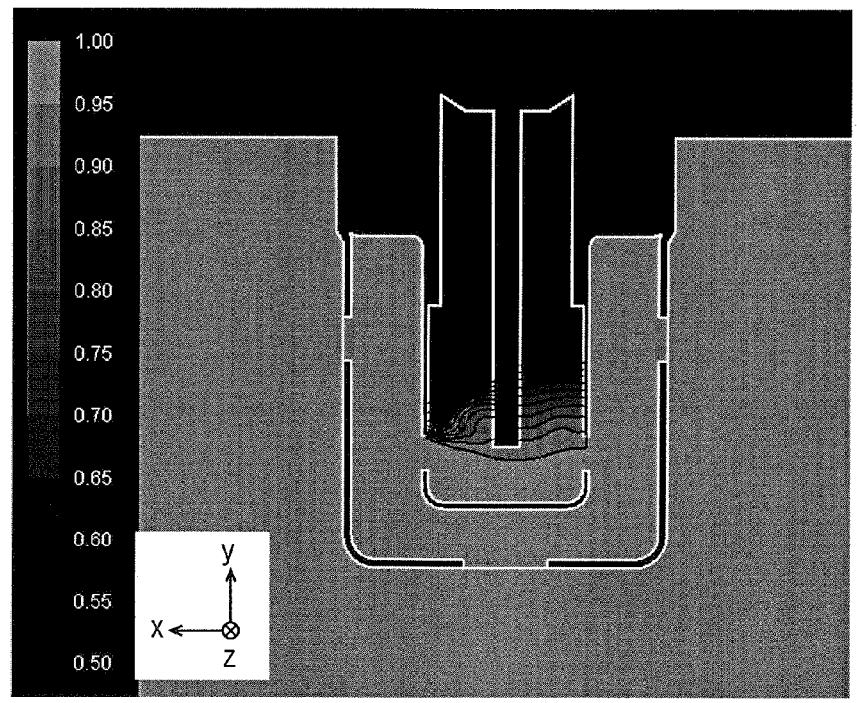

FIG. 1 is a partial cross-sectional view schematically illustrating one example of a configuration of a gas sensor 100 according to the preferred embodiment. The gas sensor 100 mainly has a sensor element 101 that detects a predetermined gas component (NOx or $O_2$) in a measurement gas and measures its concentration, and a protective cover 102 that is provided so as to surround a front end of the sensor element 101. The measurement of the concentration of the predetermined gas component in the measurement gas is performed for a measurement gas taken into the sensor element 101 via the protective cover 102 from the outside of the gas sensor 100.

The protective cover 102 is adopted in order to not only effectively prevent adhesion of water to the sensor element 101 and intrusion of water into the sensor element 101, but also secure high responsiveness for the gas sensor 100.

The preferred embodiment describes the case where the gas sensor 100 is a NOx sensor that detects nitrogen oxide (NOx) as an example.

<Schematic Configuration of the Sensor Element>

First, a description will be made of a schematic configuration of a gas sensor 100.

FIG. 2 is a schematic cross-sectional view schematically showing one example of the configuration of the sensor element 101. A sensor 101 is an elongated element of a plate-shaped configuration having a structure in which six layers of a first substrate layer 1, a second substrate layer 2, a third substrate layer 3, a first solid electrolyte layer 4, a spacer layer 5, and a second solid electrolyte layer 6 are laminated in this order from the lower side in the drawing, each of the layers being composed of an oxygen ion conducting solid electrolyte layers such as zirconia ($ZrO_2$). In addition, the solid electrolyte configuring those six layers is densely airtight. The sensor element 101 is provided in such a manner that after a predetermined process and printing of a circuit pattern are performed on a ceramic green sheet corresponding to each layer, they are laminated and integrated by baking.

A gas inlet 10, a first diffusion-controlling part 11, a buffer space 12, a second diffusion-controlling part 13, a first inner space 20, a third diffusion-controlling part 30, and a second inner space 40 are adjacently formed so as to be communicated in this order between a lower surface of the second solid electrolyte layer 6 and an upper surface of the first solid electrolyte layer 4, at one end of the sensor element 101.

The gas inlet 10, the buffer space 12, the first inner space 20, and the second inner space 40 are internal spaces provided by hollowing the spacer layer 5 in the sensor element 101, in which their upper parts are defined by the lower surface of the second solid electrolyte layer 6, their lower parts are defined by the upper surface of the first solid electrolyte layer 4, and their side parts are defined by a side surface of the spacer layer 5.

Each of the first diffusion-controlling part 11, the second diffusion-controlling part 13, and the third diffusion-controlling part 30 is provided as two horizontally long (an opening has a longitudinal direction in a direction perpendicular to the drawing) slits. In addition, a portion from the gas inlet 10 to the second inner space 40 is also referred to as a gas distribution part.

In addition, in a position more distant from the end side than the gas distribution part, a reference gas inlet space 43 is provided between an upper surface of the third substrate layer 3 and a lower surface of the spacer layer 5, in which its side part is defined by a side surface of the first solid electrolyte layer 4. For example, the air is introduced to the reference gas inlet space 43 as a reference gas in measuring the NOx concentration.

An air inlet layer 48 is composed of porous alumina, and the reference gas is introduced to the air inlet layer 48 through the reference gas inlet space 43. In addition, the air inlet layer 48 is formed to cover a reference electrode 42.

The reference electrode 42 is formed so as to be sandwiched between the upper surface of the third substrate layer 3 and the first solid electrolyte layer 4, and as described above, the air inlet layer 48 leading to the reference gas inlet space 43 is provided around the reference electrode 42. In addition, as will be described below, an oxygen concentration (oxygen partial pressure) in the first inner space 20 or the second inner space 40 can be measured using the reference electrode 42.

The gas inlet 10 is a portion open to an external space in the gas distribution part, and a measurement gas is introduced from the external space into the sensor element 101 through the gas inlet 10.

The first diffusion-controlling part 11 is a portion to apply a predetermined diffusion resistance to the measurement gas which is brought in from the gas inlet 10.

The buffer space 12 is a space provided to guide the introduced measurement gas from the first diffusion-controlling part 11 to the second diffusion-controlling part 13.

The second diffusion-controlling part 13 is a portion to apply a predetermined diffusion resistance to the measurement gas which is introduced from the buffer space 12 to the first inner space 20.

When the measurement gas is introduced from the outside the sensor element 101 to the first inner space 20, the measurement gas which was abruptly introduced from the gas inlet 10 into the sensor element 101 due to pressure fluctuation of the measurement gas in the outer space (pulsation of exhaust pressure in the case that the measurement gas is an exhaust gas of a car) is not directly introduced into the first inner space 20 but introduced into the first inner space 20 after the concentration fluctuation of the measurement gas has been negated through the first diffusion-controlling part 11, the buffer space 12, and the second diffusion-controlling part 13. Accordingly, the concentration fluctuation of the measurement gas is negligibly small when the gas is introduced to the first internal space.

The first inner space 20 is provided as a space to adjust an oxygen partial pressure in the measurement gas which has been introduced through the second diffusion-controlling part 13. The oxygen partial pressure is adjusted by an operation of a main pump cell 21.

The main pump cell 21 is an electrochemical pump cell including an inner pump electrode 22 having a ceiling electrode part 22a provided on almost all over the lower surface of the second solid electrolyte layer 6 which faces the first inner space 20, an outer pump electrode 23 provided on the upper surface of the second solid electrolyte layer 6 so as to be exposed to the external space and opposed to the ceiling electrode part 22a, and the second solid electrolyte layer 6 sandwiched between the above electrodes.

The inner pump electrode 22 lie astride the upper and lower solid electrolyte layers (second solid electrolyte layer 6 and the first solid electrolyte layer 4) to define the first inner space 20, and the spacer layer 5 to define the side wall thereof. More specifically, the ceiling electrode part 22a is formed on the lower surface of the second solid electrolyte layer 6 to define a ceiling surface of the first inner space 20, a bottom electrode part 22b is formed on the upper surface of the first solid electrolyte layer 4 to define a bottom surface thereof, and a side electrode part (not shown) is formed on a side wall surface (inner surface) of the spacer layer 5 to define each side wall of the first inner space 20, so as to connect the ceiling electrode part 22a to the bottom electrode part 22b, so that a structure having a tunnel configuration at the portion of the side electrode part is provided.

Each of the inner pump electrode 22 and the outer pump electrode 23 is formed as a porous cermet electrode (cermet electrode including Pt containing Au by 1% and zirconia). However, the inner pump electrode 22 which is in contact with the measurement gas is formed of a material whose reducing ability with respect to NOx component in the measurement gas is weakened. The inner pump electrode 22 will be described in detail below.

The main pump cell 21 can pump out the oxygen in the first inner space 20 to the external space, or pump in the oxygen in the external space into the first inner space 20 by means of applying a desired pump voltage $Vp0$ between the inner pump electrode 22 and the outer pump electrode 23 so as to generate a pump current $Ip0$ in a positive direction or negative direction between the inner pump electrode 22 and the outer pump electrode 23.

Moreover, in order to detect the oxygen concentration (oxygen partial pressure) in the atmosphere of the first inner space 20, an electrochemical sensor cell, that is, a main-pump-controlling oxygen-partial-pressure detection sensor cell 80 includes the inner pump electrode 22, the second solid electrolyte layer 6, the spacer layer 5, the first solid electrolyte layer 4, the third substrate layer 3, and the reference electrode 42.

The oxygen concentration (oxygen partial pressure) in the first inner space 20 can be found by measuring an electromotive force $V0$ in the main-pump-controlling oxygen-partial-pressure detection sensor cell 80. Furthermore, the pump current $Ip0$ is controlled by feedback-controlling the $Vp0$ to keep the electromotive force constant. Thus, the oxygen concentration in the first inner space 20 can be kept at a predetermined value.

The first diffusion-controlling part 30 is a portion to apply a predetermined diffusion resistance to the measurement gas whose oxygen concentration (oxygen partial pressure) has been controlled in the first inner space 20 by the operation of the main pump cell 21, and introduces the measurement gas to the second inner space 40.

The second inner space 40 is provided to perform an operation regarding the measurement of a nitrogen oxide (NOx) concentration in the measurement gas which has been introduced through the third diffusion-controlling part 30. The NOx concentration is mainly measured in the second inner space 40 whose oxygen concentration has been adjusted by an auxiliary pump cell 50, by an operation of a measurement pump cell 41.

After the oxygen concentration (oxygen partial pressure) has been previously adjusted in the first inner space 20, the oxygen partial pressure of the measurement gas which has been introduced through the third diffusion-controlling part is further adjusted by the auxiliary pump cell 50 in the second inner space 40. Therefore, since the oxygen concentration in the second inner space 40 can be kept constant with a high degree of accuracy, the gas sensor 100 can measure the NOx concentration with a high degree of accuracy.

The auxiliary pump cell 50 is an auxiliary electrochemical pump cell including an auxiliary pump electrode 51 having a ceiling electrode part 51a provided on almost a whole lower surface of the second solid electrolyte layer 6 which faces the second inner space 40, the outer pump electrode 23 (not limited to the outer pump electrode 23 but may be an appropriate electrode positioned outside the sensor element 101), and the second solid electrolyte layer 6.

The auxiliary pump electrode 51 is provided in the second inner space 40 so as to have a tunnel structure similar to the inner pump electrode 22 provided in the first inner space 20. That is, the ceiling electrode part 51a is formed on the second solid electrolyte layer 6 defining a ceiling surface of the second inner space 40, a bottom electrode part 51b is formed on the first solid electrolyte layer 4 defining a bottom surface of the second inner space 40, and a side electrode part (not shown) to connect the ceiling electrode part 51a to the bottom electrode part 51b is provided on each wall surface of the spacer layer 5 defining a side wall of the second inner space 40.

In addition, the auxiliary pump electrode 51 is also formed of a material whose reducing ability with respect to the NOx component in the measurement gas is weakened, similar to the inner pump electrode 22.

The auxiliary pump cell 50 can pump out the oxygen in the atmosphere of the second inner space 40 to the external space, or pump in the oxygen in the external space into the second inner space 40 by means of applying a desired pump voltage $Vp1$ between the auxiliary pump electrode 51 and the outer pump electrode 23.

Moreover, in order to control the oxygen partial pressure in the atmosphere of the second inner space 40, an auxiliary-pump-controlling oxygen-partial-pressure detection sensor cell 81 includes the auxiliary pump electrode 51, the reference electrode 42, the second solid electrolyte layer 6, the spacer layer 5, the first solid electrolyte layer 4, and the third substrate layer 3.

In this regard, the auxiliary pump cell 50 is pumped by a variable power supply 52 whose voltage is controlled based on an electromotive force $V1$ detected by the auxiliary-pump-controlling oxygen-partial-pressure detection sensor cell 81. Thus, the oxygen partial pressure in the atmosphere of the second inner space 40 can be lowered so as not to substantially affect the measurement of NOx.

In addition, at the same time, its pump current $Ip1$ is used to control the electromotive force of the main-pump-controlling oxygen-partial-pressure detection sensor cell 80. More specifically, the pump current $Ip1$ is inputted to the main-pump-controlling oxygen-partial-pressure detection sensor cell 80 as a control signal and then its electromotive force $V0$ is controlled, so that an inclination of the oxygen partial pressure in the measurement gas which is introduced from the third diffusion-controlling part 30 to the second inner space 40 is controlled to be always kept constant. When used as the NOx sensor, the oxygen concentration in the second inner space 40 is kept at a constant value such as about 0.001 ppm, by the operations of the main pump cell 21 and the auxiliary pump cell 50.

The measuring pump cell 41 measures the NOx concentration in the measurement gas, in the second inner space 40. The measuring pump cell 41 is an electrochemical pump cell including a measurement electrode 44 provided on the upper surface of the first solid electrolyte layer 4 which faces the second inner space 40 so as to be apart from the third diffusion-controlling part 30, the outer pump electrode 23, the second solid electrolyte layer 6, the spacer layer 5, and the first solid electrolyte layer 4.

The measurement electrode 44 is a porous cermet electrode which has an almost-rectangular shape in a plan view. The measurement electrode 44 also functions as a NOx reducing catalyst to reduce NOx existing in the atmosphere of the second inner space 40. Furthermore, the measurement electrode 44 is covered with a fourth diffusion-controlling part 45.

The fourth diffusion-controlling part 45 is a film made of a porous body mostly including alumina ($Al_2O_3$). The fourth diffusion-controlling part 45 takes a roll in limiting a NOx amount flowing into the measurement electrode 44, and also functions as a protection film of the measurement electrode 44.

The measuring pump cell 41 pumps out the oxygen generated due to decomposition of the nitrogen oxide in the atmosphere around the measurement electrode 44, and can detect its generation amount as a pump current Ip2.

Moreover, in order to detect an oxygen partial pressure around the measurement electrode 44, an electrochemical sensor cell, that is, a measuring-pump-controlling oxygen-partial-pressure detection sensor cell 82 includes the second solid electrolyte layer 6, the spacer layer 5, the first solid electrolyte layer 4, the third substrate layer 3, the measurement electrode 44, and the reference electrode 42. A variable power supply 46 is controlled based on a control voltage V2 detected by the measuring-pump-controlling oxygen-partial-pressure detection sensor cell 82.

The measurement gas which has been introduced in the second inner space 40 reaches the measurement electrode 44 through the fourth diffusion-controlling part 45 under the condition that its oxygen partial pressure is controlled. The nitrogen oxide in the measurement gas around the measurement electrode 44 is reduced and oxygen is generated ($2NO \rightarrow N_2 + O_2$). Thus, the generated oxygen is pumped by the measuring pump cell 41, and at this time a voltage Vp2 of the variable power supply is controlled so that the control voltage V2 detected by the measuring-pump-controlling oxygen-partial-pressure detection sensor cell 82 can be kept constant. Since the amount of oxygen generated around the measurement electrode 44 is proportional to the concentration of the nitrogen oxide in the measurement gas, the concentration of the nitrogen oxide in the measurement gas is calculated using the pump current Ip2 in the measuring pump cell 41.

In addition, if oxygen partial pressure detecting means is provided by combining the measurement electrode 42, the first solid electrolyte layer 4, the third substrate layer 3, and the reference electrode 44, as an electrochemical sensor cell, an electromotive force can be detected based on a difference between the oxygen amount generated due to the reduction of the NOx component in the atmosphere around the measurement electrode 44 and an oxygen amount in the reference air, and as a result, the concentration of the NOx component in the measurement gas can be found.

What is more, an electrochemical sensor cell 83 is constituted of the second solid electrolyte layer 6, the spacer layer 5, the first solid electrolyte layer 4, the third substrate layer 3, the outer pump electrode 23, and the reference electrode 42, and the oxygen partial pressure in the measurement gas outside the sensor can be detected by an electromotive force Vref obtained by this sensor cell 83.

In the gas sensor 100 having the above configuration, the measurement gas whose oxygen partial pressure is always kept at a constant low value (which does not affect the measurement of NOx substantially) by the operations of the main pump cell 21 and the auxiliary pump cell 50 is applied to the measuring pump cell 41. Therefore, the NOx concentration in the measurement gas can be known, based on the pump current Ip2 which flows on the basis that the oxygen generated by the reduction of NOx is pumped out by the measuring pump cell 41, in approximately proportion to the NOx concentration in the measurement gas.

Furthermore, in order to enhance oxygen ion conductivity of the solid electrolyte, the sensor element 101 has a heater part 70 taking a role of temperature regulation to heat the sensor element 101 and keep its temperature. The heater part 70 includes heater electrodes 71a and 71b, a heater 72, a through hole 73, a heater insulation layer 74, and a pressure diffusion hole 75.

The heater electrodes 71a and 71b are an electrode formed to be in contact with the lower surface of the first substrate layer 1. When the heater electrodes 71a and 71b are connected to an external power supply, a power can be supplied to the heater part 70 from the outside.

The heater 72 is an electric resistor formed to be sandwiched between the second substrate layer 2 and the third substrate layer 3 vertically. The heater 72 is connected to the heater electrode 71 through the through hole 73, and generates heat when a power is supplied from the outside through the heater electrode 71, and heats the solid electrolyte forming the sensor element 101 and keeps its temperature.

Then, the heater 72 is buried all over the region from the first inner space 20 to the second inner space 40, and can regulate the temperature in the whole sensor element 101 so that the solid electrolyte can be activated.

The heater insulation layer 74 is formed of an insulator such as alumina, on upper and lower surfaces of the heater 72. The heater insulation layer 74 is formed with a view to obtaining electric insulation between the second substrate layer 2 and the heater 72, and electric insulation between the third substrate layer 3 and the heater 72.

The pressure diffusion hole 75 is a portion configured to penetrate the third substrate layer 3 and communicate with the reference gas inlet space 43, and formed with a view to lessening an inner pressure from rising with the temperature rise in the heater insulation layer 74.

<Schematic Configuration of Protective Cover>

A schematic configuration of the protective cover 102 is described below with reference to FIG. 1. For convenience of the description, FIG. 1 illustrates an xyz orthogonal coordinate system in which a right-left direction in the drawing is an x axial direction, an up-down direction in the drawing is a y axial direction, and a direction perpendicular to the paper surface is a z axial direction. Further, FIG. 1 illustrates the gas sensor 100 so that a longitudinal direction of the sensor element 101 matches with the y axial direction.

The protective cover 102 has an internal protective cover 110 provided to surround a front end 101a of the sensor element 101, and an outer protective cover 120 provided to surround the inner protective cover 110. That is, the protective cover 102 according to the preferred embodiment adopts a double structure composed of the inner protective cover 110 and the outer protective cover 120.

The inner protective cover 110 and the outer protective cover 120 are bottomed cylindrical members made of metal or the like. In addition, the inner protective cover 110 has a flange part 112 at an end on a side of the y axial positive direction. The flange part 112 has a first bent part 112a bent to the x axial direction from a cylindrical portion extending to the y axial direction, and a second bent part 112b further bent to the y axial direction from the first bent part 112a. When the second bend part 112b abuts on or fits into the outer protective cover 120, the inner protective cover 110 is fixed to the outer protective cover 120. Further, a housing 103 is fitted into an opening of the outer protective cover 120, and the outer protective cover 120 is fixed to the housing 103 by spot welding or the like.

The inner protective cover 110 and the outer protective cover 120 are provided with a plurality of approximately (i.e., substantially) circular gas distributing holes in order to introduce or exhaust the measurement gas to the inside or to the outside. As the gas distributing holes, square holes, slits and flap-structured holes may be adopted, and such shapes can produce the effect similar to the case of the approximately circular distributing holes.

A side surface of the inner protective cover 110 has a plurality of inner gas distributing holes 111 formed on two rows (formed so as to be separated in the y axial direction) in the longitudinal direction of the sensor element 101. FIG. 1 illustrates the case where the inner gas distributing holes 111 include six first inner gas distributing holes 111a and six second inner gas distributing holes 111b. The first inner gas distributing holes 111a are formed on a position toward a y axial negative direction than the sensor element front end 101a on a side surface (cylindrical portion) of the inner protective cover 111 (a bottom side of the inner protective cover 110 with respect to a position opposed to the sensor element front end 101a). The second inner gas distributing holes 111b are formed on a position in the y axial positive direction with respect to the sensor element front end 101a (the other front end side of the sensor element 101 with respect to the position opposed to the sensor element front end 101a).

A side surface of the outer protective cover 120 has a plurality of first outer gas distributing holes 121. FIG. 1 illustrates the case where a number of the first outer gas distributing holes 121 is six. A bottom portion of the outer protective cover 120 has one second outer gas distributing hole 122.

The first outer gas distributing holes 121 are formed on a side surface of the outer protective cover 120 (the cylindrical portion extending to the y axial direction) between a position opposed to the first inner gas distributing holes 111a and a position opposed to the second inner gas distributing holes 111b.

That is, the first inner gas distributing holes 111a, the first outer gas distributing holes 121 and the second inner gas distributing holes 111b are formed in this order in the y axial positive direction.

With such an arrangement relationship in the y axial positive direction, most of water that enters the outer protective cover 120 through the first outer gas distributing holes 121 collides with or adheres to the side surface of the inner protective cover 110. This prevents the water from reaching the inside of the inner protective cover 110 and adhering to the sensor element 101, or prevents the water from intruding the sensor element 101.

Further, the water that collides with or adheres to the inner protective cover 110 does not remain in the outer protective cover 120, and is exhausted to the outside through the second outer gas distributing hole 122. As a result, in the gas sensor 100 according to the preferred embodiment, water resistance that does not practically become problem is secured.

As described above, since the gas sensor 100 according to the preferred embodiment has the inner gas distributing holes 111 at two up and down rows on the side surface of the inner protective cover 110, a number of distributing routes for introducing the measurement gas into the inner protective cover and exhausting the measurement gas to the outside is larger than that in a gas sensor having only one row of the inner gas distributing holes. As a result, a replacement property of the measurement gas in the protective cover 102 is improved.

Further, in the longitudinal direction of the sensor element 101, the sensor element front end 101a is arranged between the first inner gas distributing holes 111a and the second inner gas distributing holes 111b. For this reason, particularly the replacement property of the measurement gas around the sensor element front end 101a is excellent.

FIGS. 3 to 8 are diagrams illustrating simulation results of a temporal change in a replacement rate of the measurement gas in the protective cover 102 when the measurement gas is introduced into the protective cover 102 from the outside in order to confirm the replacement property of the measurement gas in the protective cover 102 described above. The gas replacement rate is a percentage of the measurement gas in gases in the inner protective cover 110. The simulation is run on three gas sensors A, B and C shown in Table 1 in which forms of the inner gas distributing holes 111 in the inner protective cover 110 are different. The measurement gas has the constant NOx concentration that is different from that of the gas in the protective cover 102.

TABLE 1

| | | Gas Sensor A | Gas Sensor B | Gas Sensor C |
|---|---|---|---|---|
| Inner Protective Cover | Diameter of First Inner Gas Distributing Hole (Lower Hole) | 1.0 mm | 1.0 mm | 1.5 mm |
| | Diameter of Second Inner Gas Distributing Hole (Upper Hole) | 1.0 mm | 0.5 mm | — |
| | Lower Hole Area/Upper Hole Area (S-low/S-high) | 1.00 | 4.00 | — |
| Outer Protective Cover | Diameter of First Outer Gas Distributing Hole | 2.0 mm | 2.0 mm | 2.0 mm |

The gas sensors A and B have the six first inner gas distributing holes 111a and the six second inner gas distributing holes 111b on two up and down rows on the side surface of the inner protective cover 110. As shown in Table 1, in the gas sensor A, a diameter (1.0 mm) of the first inner gas distributing holes 111a is the same as a diameter (1.0 mm) of the second inner gas distributing holes 111b. In the gas sensor B, a diameter (0.5 mm) of the second inner gas distributing holes 111b is smaller than a diameter (1.0 mm) of the first inner gas distributing holes 111a, and a total opening area of the first inner gas distributing holes 111a/a total opening area of the second inner gas distributing holes 111b (S-low/S-high) is 4.0. On the other hand, the gas sensor C has the 6 inner gas distributing holes on one row on the side surface of the inner protective cover.

FIGS. 3 to 7 are diagrams illustrating distribution of the gas replacement rate in the protective cover 102 in the simulation on the gas sensors A and C. FIG. 3A, FIG. 4A, FIG. 5A, FIG. 6A, and FIG. 7A are diagrams illustrating the gas sensor A, and FIG. 3B, FIG. 4B, FIG. 5B, FIG. 6B, and FIG. 7B are diagrams illustrating the gas sensor C. The time and replacement rate shown in the drawings represent the gas replacement rate around the sensor element front end 101a obtained by the simulation after a predetermined time elapses. For example, in FIG. 3A, the gas around the sensor element front end 101a includes the measurement gas of 65% after 20 ms elapses.

As shown in FIGS. 3 to 7, in the gas sensor A, a stagnant area where the introduction of the measurement gas is difficult is hardly formed, and the gas in the inner protective cover is replaced by the measurement gas as the time passes. On the other hand, in the gas sensor C, a stagnant area is formed on a place closer to the flange side than the sensor element front end 101a, and the replacement by the measurement gas in the inner protective cover is hindered even after time passes in that area.

That is, the gas sensor A having the inner gas distributing holes 111 on the two up and down rows has more distributing routes for introducing the measurement gas into the inner protective cover 110 and exhausting the measurement gas to the outside than the gas sensor C having only one row of the inner gas distributing holes. As a result, the gas sensor A has the excellent replacement property of the measurement gas in the inner protective cover 110.

FIG. 8 is a diagram illustrating a temporal change in the gas replacement rate around the sensor element front end 101a in the protective cover 102 of each of the gas sensors A, B and C obtained by the simulation.

As shown in FIG. 8, the time required for the replacement rate of the measurement gas around the sensor element front end 101a reaching 90% is about 50 msec in the gas sensor A, about 80 msec in the gas sensor B, and about 100 msec in the gas sensor C.

The time required for the replacement rate of the measurement gas around the sensor element front end 101a reaching 100% is about 70 msec in the gas sensor A, and about 150 msec in the gas sensor B. On the other hand, the replacement rate of the measurement gas around the sensor element front end 101a in the gas sensor C does not reach 100% even at the time point at which 200 msec elapses.

That is, in the gas sensors A and B having the inner gas distributing holes 111 on the two up and down rows, the gas around the sensor element front end 101a is replaced for a shorter time than the gas sensor C having only one row of the inner gas distributing holes.

With the above gas replacement property, the gas sensor 100 according to the preferred embodiment has excellent responsiveness.

A more preferred configuration of the protective cover 102 is described below.

The first inner gas distributing holes 111a and the second inner gas distributing holes 111b are preferably formed at regular intervals on a predetermined side peripheral position of the inner protective cover 110 parallel with the bottom portion of the inner protective cover 110.

Similarly, the first outer gas distributing holes 121 are preferably formed at regular intervals on a predetermined side peripheral position of the outer protective cover 120 parallel with the bottom portion of the outer protective cover 120.

The number of the first inner gas distributing holes 111a is preferably the same as the number of the second inner gas distributing holes 111b. The first inner gas distributing holes 111a and the second inner gas distributing holes 111b are preferably formed so that a line for straightly connecting a center position of the first inner gas distributing holes 111a and a corresponding center position of the second inner gas distributing holes 111b becomes parallel with an axial direction (y axial direction) of the inner protective cover 111.

With such a configuration of the protective cover 102, the measurement gas is avoided from being intensively introduced or exhausted into or from any of the gas distributing holes in the gas sensor 100. As a result, the replacement property of the measurement gas in the protective cover 102 in the gas sensor 100 is further improved. Furthermore, a local temperature fluctuation in the sensor element 101 is prevented, and thus generation of cracks on the sensor element due to the temperature fluctuation is effectively prevented.

It is preferable that the total opening area of the first inner gas distributing holes 111a/the total opening area of the second inner gas distributing holes 111b (S-low/S-high) is 3.0 or less. When S-low/S-high is 3.0 or less, the gas sensor 100 can be provided with the waterproofness that does not practically cause problem.

Particularly when the S-low/S-high of the first inner gas distributing holes 111a is 0.44 or less, the gas sensor 100, that has the waterproofness equivalent to that of a gas sensor having only one row of the inner gas distributing holes on the side surface of the inner protective cover and has higher responsiveness, is realized.

Since the gas sensor 100 according to the preferred embodiment has the inner gas distributing holes 111 on the two up and down rows on the side surface of the inner protective cover 110, the responsiveness is excellent, and the adhesion of water to the sensor element 101 and the intrusion of water into the sensor element 101 can be effectively prevented.

Since the gas sensor 100 according to the preferred embodiment uses the protective cover 102 having the double structure, the manufacturing steps are further simplified and the manufacturing cost is further reduced in comparison with protective covers having the triplex structure.

EXAMPLE

Results of testing the gas sensor 100 according to the preferred embodiment and a gas sensor conventionally used are described below.

As an example, a responsiveness test and a waterproofness test were conducted on gas sensors "a" through "e" shown in Table 2. The gas sensors "a" to "e" have a configuration where only the protective covers 102 are different, and the other parts of the configuration are the same as each other.

TABLE 2

|  |  | Gas Sensor a | Gas Sensor b | Gas Sensor c | Gas Sensor d | Gas Sensor e |
|---|---|---|---|---|---|---|
| Inner Protective Cover | Diameter of First Inner Gas Distributing Hole (Lower Hole) | 1.0 mm | 1.0 mm | 1.0 mm | 1.0 mm | 1.5 mm |

TABLE 2-continued

|  |  | Gas Sensor a | Gas Sensor b | Gas Sensor c | Gas Sensor d | Gas Sensor e |
|---|---|---|---|---|---|---|
|  | Diameter of Second Inner Gas Distributing Hole (Upper Hole) | 1.5 mm | 1.0 mm | 0.75 mm | 0.55 mm | — |
|  | Lower Hole Area/Upper Hole Area (S-low/S-high) | 0.44 | 1.00 | 1.78 | 4.00 | — |
| Outer Protective Cover | Diameter of First Outer gas Distributing Hole | 2.0 mm | 2.0 mm | 2.0 mm | 2.0 mm | 2.0 mm |

As shown in Table 2, the gas sensors "a" through "d" have the inner gas distributing holes 111 on the two up and down rows including the six first inner gas distributing holes 111a and the six second inner gas distributing holes 111b on the side surface of the inner protective cover 110. In the gas sensors "a" through "d", the diameters (1.0 mm) of the first inner gas distributing holes 111a are the same, and the diameters of the second inner gas distributing holes 111b are 1.5 mm, 1.0 mm, 0.75 mm and 0.5 mm. Accordingly, their S-low/S-high are 0.44, 1.0, 1.78 and 4.0. On the other hand, the gas sensor "e" has the six inner gas distributing holes on one row on the side surface of the inner protective cover.

As the responsiveness test, when the NOx concentration in a mixed gas to be introduced into the protective cover 102 is changed from 0% to 100%, the time (response time) from the time point at which a sensor output (Ip2) corresponding to the NOx concentration of 10% is detected to the time point at which a sensor output (Ip2) corresponding to the NOx concentration of 90% is detected was measured at 30 times in each of the gas sensors. The NOx concentration of 70 ppm was regarded as 0%, and the NOx concentration of 500 ppm was regarded as 100%. The responsiveness was tested under the conditions that the temperature is 350° C., a gas flow rate is 10 m/s, a λ value (air excess ratio) obtained by controlling an air-fuel ratio (the oxygen concentration in the measurement gas) is 1.3.

Figure 9:
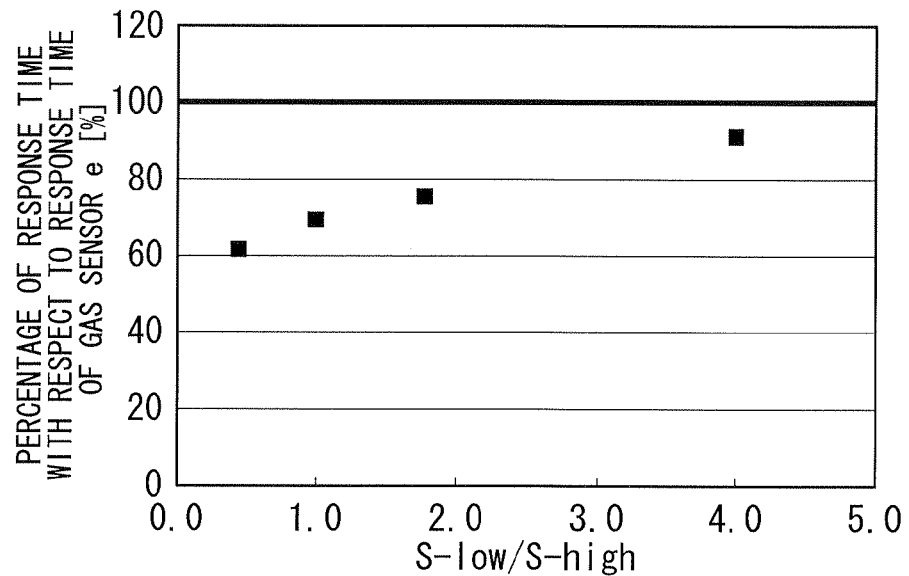
FIG. 9 is a diagram illustrating a test result of the responsiveness of the gas sensor.

The result of the responsiveness test is shown in FIG. 9. As shown in FIG. 9, when the response time of the gas sensor "e" is set to 100%, the response time of the gas sensor "a" is about 60%, the response time of the gas sensor "b" is about 70%, the response time of the gas sensor "c" is about 75%, and the response time of gas sensor "d" is about 90%.

That is, the response time of the gas sensors "a" to "d" is shorter than that of the gas sensor "e". As a result, it is confirmed that when the inner gas distributing holes 111 are provided on two up and down rows on the side surface of the inner protective cover 110 so that the number of the gas circulating routes is increased, this is effective for improving the responsiveness. It is confirmed that particularly the larger diameter of the second inner gas distributing holes 111b than the diameter of the first inner gas distributing holes 111a is more effective for improving the responsiveness.

As to the waterproof test, the quantity of water at the time when the sensor element 101 starts to break was measured at 30 times in each of the gas sensors by using a broken-out water quantity measuring device 400.

Figure 10:
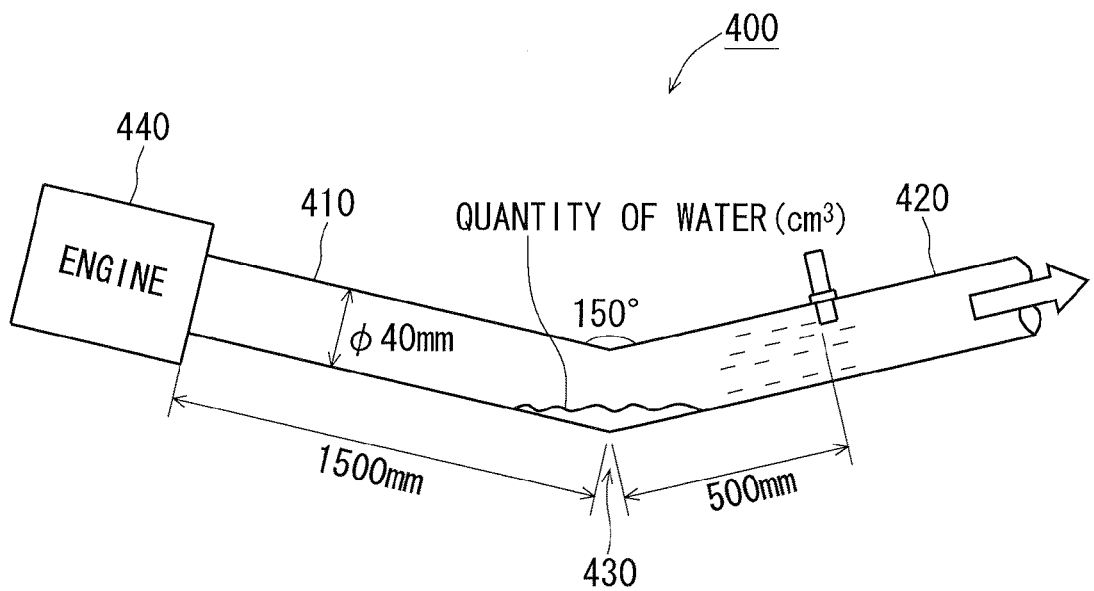
FIG. 10 is a diagram schematically illustrating a configuration of a broken-out water volume measuring device.

FIG. 10 is a diagram schematically illustrating a configuration of the broken-out water quantity measuring device 400. The broken-out water quantity measuring device 400 has two pipes 410 and 420, an engine 440, and a sensor mounting part. The pipes 410 and 420 with diameter of 40 mm are connected so that an angle becomes 150°. The engine 440 is connected on an end opposite to the connecting part 430 of the pipe 410, at a position separated by 1500 mm from a connecting part 430 to. The sensor mounting part is formed on a position on the side surface of the pipe 420 separated by 500 mm from the connecting part 430.

The test using the broken-out water quantity measuring device 400 was conducted by mounting the gas sensor to the sensor mounting part, operating the engine with water being stored in the connecting part 430 in the pipes 410 and 420, and inspecting a fluctuation in an output from the gas sensor obtained by flying of the stored water. The engine was started to be operated 60 second after electrical connection with the heater of the gas sensor was started, an acceleration operation for 3 seconds was continuously performed three times at the time point of 15 seconds after the starting. A rotational number in an idling state was 600 rpm, and a rotational number at a peak in an accelerated state was 5000 rpm. The quantity of the stored water was increased gradually by each 10 cm³ and the similar test was conducted until an abnormal output from the gas sensor was obtained. The operation of the engine was stopped at the time when an abnormal output from the sensor element was obtained, and a quantity of the water stored at that time was regarded as a broken-out water quantity.

Figure 11:
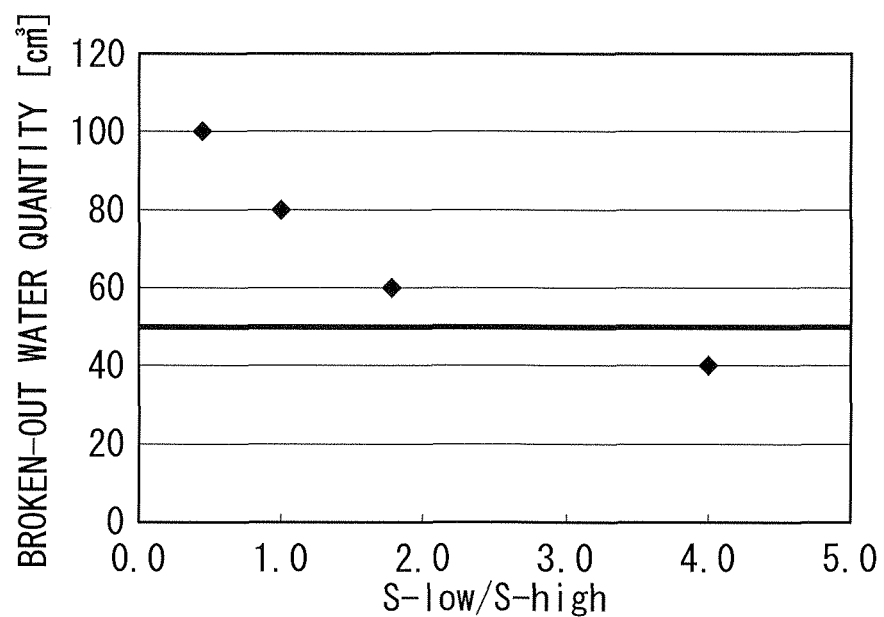
FIG. 11 is a diagram illustrating a test result of water resistance of the gas sensor.

The result of the water resistance test is shown in FIG. 11. As shown in FIG. 11, the broken-out water quantity of the gas sensor "e" is 100 cm³, and the broken-out water quantity of the gas sensor "a" is 100 cm³, the broken-out water quantity of the gas sensor "b" is 80 cm³, the broken-out water quantity of the gas sensor "c" is 60 cm³, and the broken-out water quantity of the gas sensor "d" is 40 cm³.

The waterproofness does not practically become a problem as long as the broken-out water quantity is 50 cm³ or more in the case where the waterproofness test is conducted by using the broken-out water quantity measuring device 400 under the similar conditions. That is, it is confirmed that the gas sensor "a", the gas sensor "b" and the gas sensor "c" have the waterproofness that does not practically become a problem. Particularly, the gas sensor "a" has the waterproofness equivalent to that of the gas sensor "e". Accordingly, it is recognized that it is effective for improving the responsiveness with maintaining the waterproofness to provide the inner gas distributing holes 111 whose S-low/S-high is 0.44 or less to the side surface of the inner protective cover 110.

While the invention has been shown and described in detail, the foregoing description is in all aspects illustrative and not restrictive. It is therefore understood that numerous modifications and variations can be devised without departing from the scope of the invention.

What is claimed is:

1. A gas sensor for detecting a predetermined gas component in a measurement gas, said gas sensor comprising:

A sensor element comprising solid electrolyte with oxygen ion conductivity; and

A protective cover arranged to surround said sensor element, wherein

Said protective cover includes an inner protective cover of a bottomed cylindrical shape that has a plurality of inner gas distributing holes formed in two rows on a side surface of said inner protective cover in a longitudinal direction of said sensor element and surrounds one end of said sensor element, wherein each of the plurality of inner gas distributing holes has a substantially round shape, Said plurality of inner gas distributing holes has a plurality of first inner gas distributing holes and a plurality of second inner gas distributing holes, Said plurality of first inner gas distributing holes is formed on the side surface of said inner protective cover in a position on a bottom side of said inner protective cover with respect to a position offset from one front end of said sensor element, Said plurality of second inner gas distributing holes is formed on the side surface of said inner protective cover in another position offset from said front end of said sensor element, and An outer protective cover of a bottomed cylindrical shape that has a plurality of outer gas distributing holes on a side surface of said outer protective cover and surrounds said inner protective cover, wherein each of the plurality of outer gas distributing holes has a substantially round shape, Wherein a total area of said plurality of inner gas distributing holes is determined as S1 and a total opening area of said plurality of second inner gas distributing holes is determined as S2, and $S1/S2 \leqq 0.44$.

2. The gas sensor according to claim 1, wherein
said plurality of outer gas distributing holes is formed on the side surface of said outer protective cover at a longitudinal position between the position of said plurality of first inner gas distributing holes and the position of said plurality of second inner gas distributing holes.

3. The gas sensor according to claim 2, wherein
said plurality of first inner gas distributing holes and said plurality of second inner gas distributing holes are formed at approximately regular intervals on a peripheral side of said inner protective cover.

4. The gas sensor according to claim 3, wherein
said plurality of outer gas distributing holes is formed at approximately regular intervals on a peripheral side of said outer protective cover.

5. The gas sensor according to claim 1, wherein
said plurality of first inner gas distributing holes and said plurality of second inner gas distributing holes are formed at approximately regular intervals on a peripheral side of said inner protective cover.

6. The gas sensor according to claim 5, wherein
said plurality of outer gas distributing holes is formed at approximately regular intervals on a peripheral side of said outer protective cover.

* * * * *

UNITED STATES PATENT AND TRADEMARK OFFICE
CERTIFICATE OF CORRECTION

PATENT NO. : 8,449,743 B2  
APPLICATION NO. : 12/853539  
DATED : May 28, 2013  
INVENTOR(S) : Takayuki Sekiya and Kei Kosaka Page 1 of 1

It is certified that error appears in the above-identified patent and that said Letters Patent is hereby corrected as shown below:

In the Claims:

Column 15, line 4 claim 1: change "A" to -- a --

Column 15, line 6 claim 1: change "A" to -- a --

Column 15, line 8 claim 1: change "Said" to -- said --

Column 15, line 16 claim 1: change "Said" to -- said --

Column 15, line 19 claim 1: change "Said" to -- said --

Column 15, line 24 claim 1: change "Said" to -- said --

Column 15, line 28 claim 1: change "An" to -- an --

Column 16, lines 4-5 claim 1: change "Wherein a total area of said plurality of inner gas distributing" to -- wherein a total opening area of said plurality of first inner gas distributing --

Signed and Sealed this  
Thirteenth Day of August, 2013

Teresa Stanek Rea  
*Acting Director of the United States Patent and Trademark Office*